Figure 1:
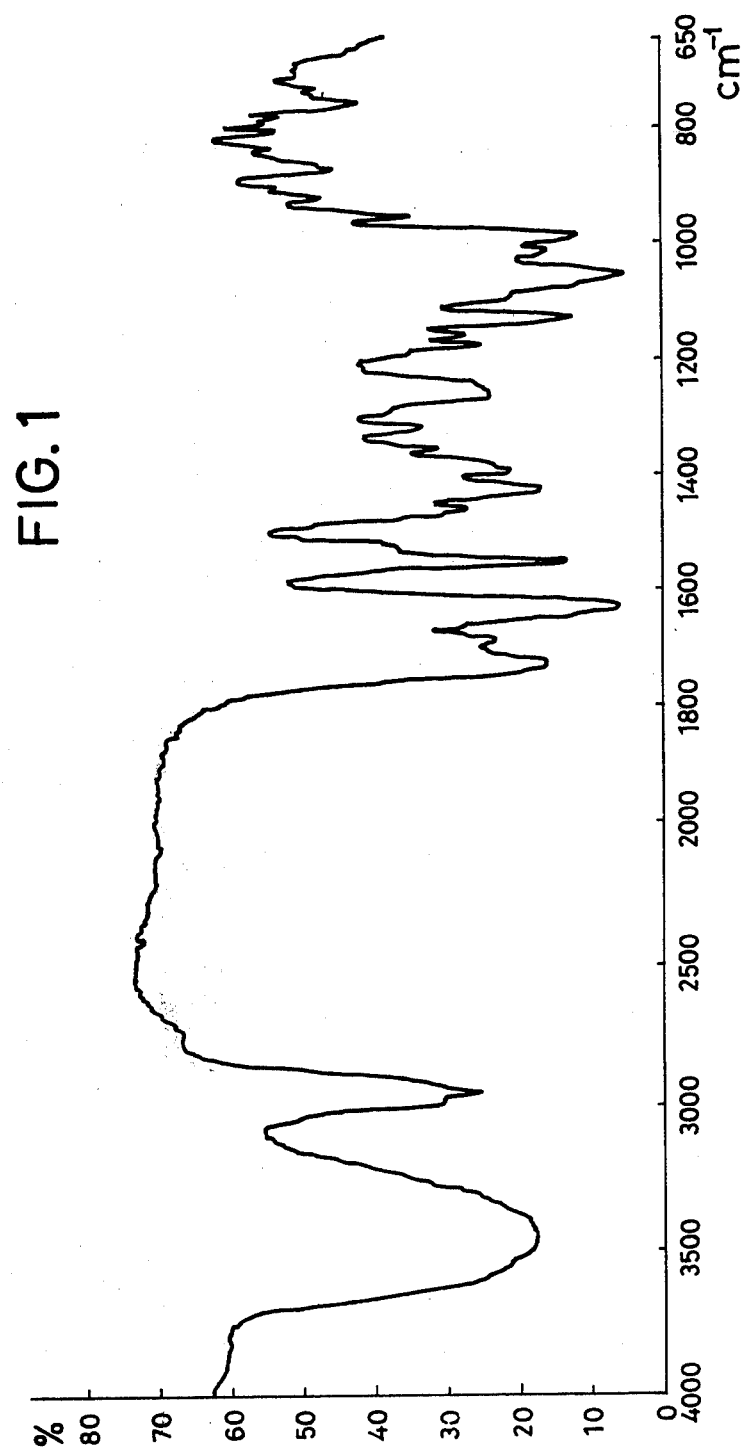

United States Patent [19]

Tomita et al.

[11] 4,346,075
[45] Aug. 24, 1982

[54] ANTIBIOTIC DC-11 AND PROCESS FOR PRODUCTION THEREOF

[75] Inventors: Fusao Tomita; Tatsuya Tamaoki; Nobuo Nakamura, all of Machida; Shuji Okubo, Matsudo; Kunikatsu Shirahata, Machida; Masaji Kasai, Fujisawa; Tetsuo Oka, Machida, all of Japan

[73] Assignee: Kyowa Hakko Kogyo Co., Ltd., Tokyo, Japan

[21] Appl. No.: 252,062

[22] Filed: Apr. 8, 1981

Related U.S. Application Data

[63] Continuation-in-part of Ser. No. 31,912, Apr. 20, 1979, abandoned.

[30] Foreign Application Priority Data

Jun. 14, 1980 [JP] Japan .................................. 55-80482
Aug. 20, 1980 [JP] Japan ................................ 55-114373
Sep. 18, 1980 [JP] Japan ................................ 55-128605

[51] Int. Cl.$^3$ ............................................. A61K 35/00
[52] U.S. Cl. .................................... 424/120; 435/169; 536/16.8
[58] Field of Search .......................... 424/120; 536/17; 435/169

[56] References Cited

PUBLICATIONS

J. of Antibiotics, vol. 33, No. 6, pp. 668–670, Jun. 1980, "Novel Antitumor Antibiotics, Tetrocarcins", F. Tomita, et al.
J. of Antibiotics, vol. 33, No. 9, pp. 940–945, Sep. 1980, "Tetrocarcins, Novel Antitumor Antibiotics", F. Tomita, et al.
J. of Antibiotics, vol. 33, Nov. 9, pp. 946–950, Sep. 1980, "Tetrocarcins, Novel Antitumor Antibiotics", T. Tamaoki, et al.
Tetrahedron Letters, vol. 21, pp. 2559–2560, 1980, "The Structure of Tetronolide . . .", Hirama, et al.
23rd Symposium Papers, pp. 584–591, Oct. 1980 (The Chemistry of Natural Product).
J. Antibiotics, vol. 33, 244–246, Feb. 1980, "A New Antibiotic, Anterlermicin A", Kobinta, et al.

*Primary Examiner*—Jerome D. Goldberg
*Attorney, Agent, or Firm*—Fitzpatrick, Cella, Harper & Scinto

[57] ABSTRACT

A new antibacterial compound, DC-11 is produced by fermentation of a microorganism belonging to the genus Micromonospora. The antibiotic is accumulated in the culture medium and is isolated therefrom.

4 Claims, 8 Drawing Figures

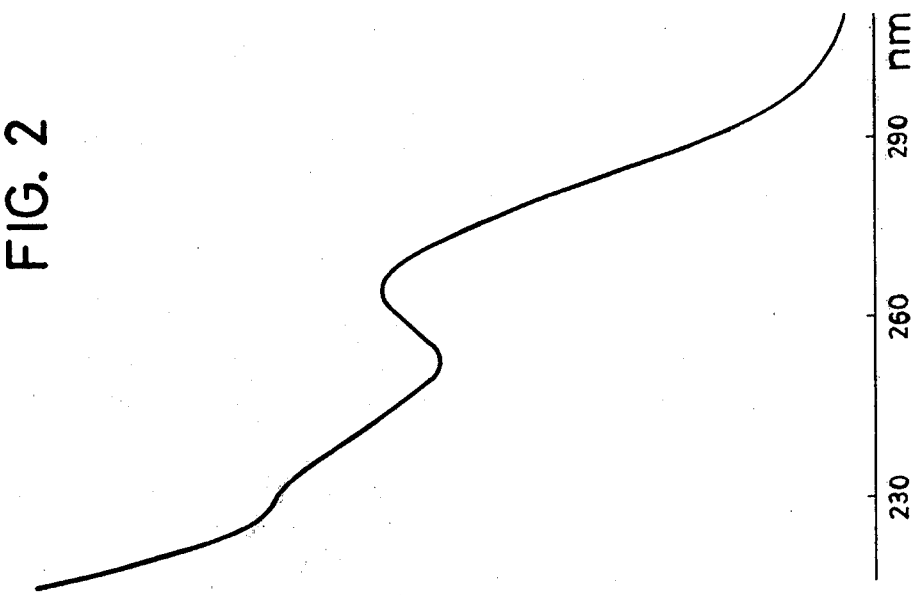

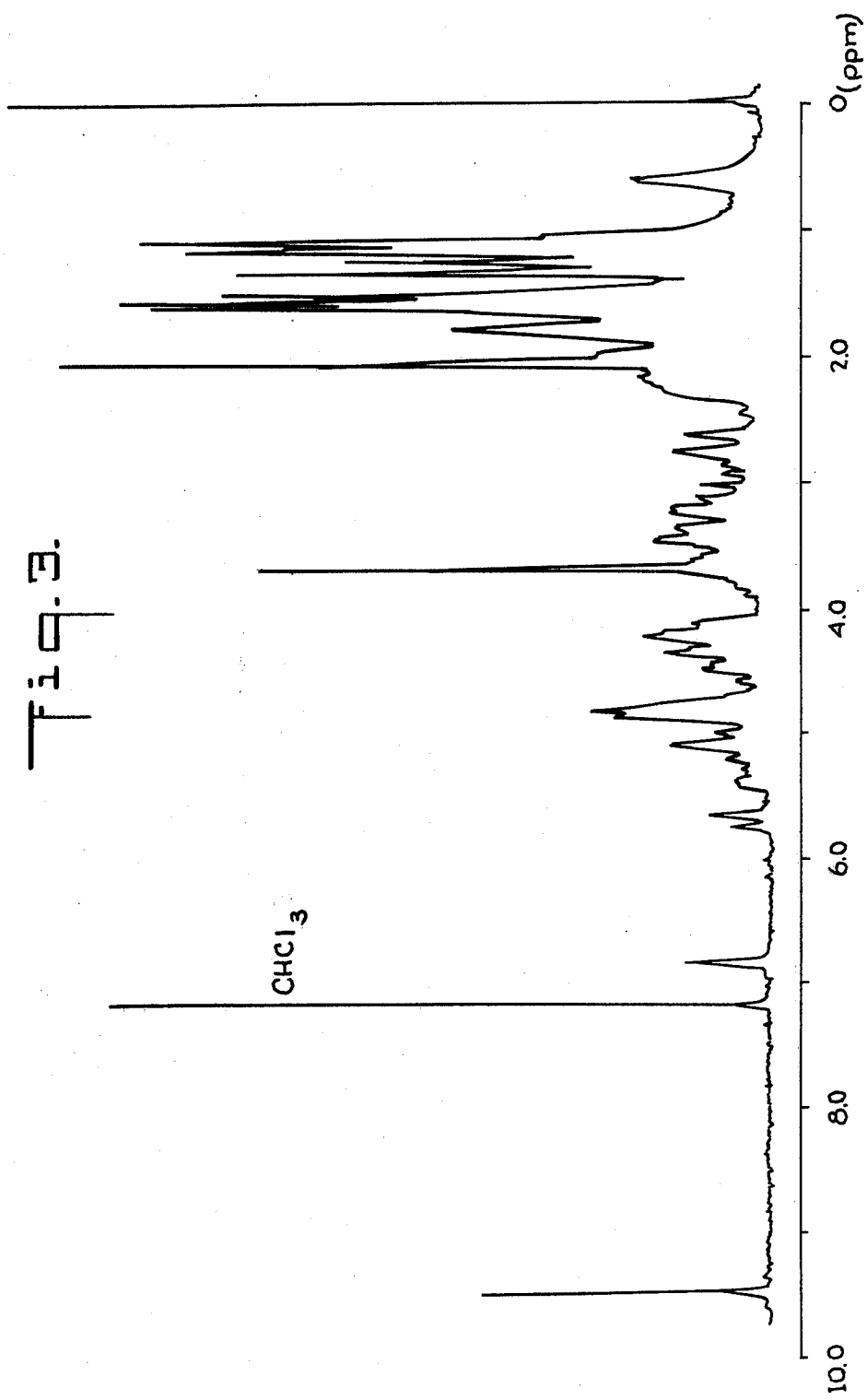

ANTIBIOTIC DC-11 AND PROCESS FOR PRODUCTION THEREOF

RELATED APPLICATIONS

This application is a continuation-in-part of our copending application Ser. No. 31,912, filed Apr. 20, 1979, now abandoned.

BACKGROUND OF THE INVENTION

The present invention relates to a new composition of matter having antibacterial activity, such composition of matter being designated DC-11. The invention also pertains to the production of DC-11 by culturing a microorganism belonging to the genus Micromonospora, which is capable of producing DC-11, in a nutrient medium, until antibacterial activity is detected in the culture liquor and then recovering DC-11 therefrom.

Compounds which have antibacterial activity are always in demand. To this end, a microorganism has been isolated from a soil sample from Sendai-shi, Miyagi-ken, Japan; and it has been found that when the strain is cultured, a compound having antibacterial activity is produced in the culture liquor. A study of the morphological properties indicates that the microorganism is a new strain belonging to the genus Micromonospora; and a study of the chemical, physical and biological properties of the active substance indicates that the composition of matter is a new compound which is designated DC-11.

SUMMARY OF THE INVENTION

In accordance with the present invention, the novel compound, DC-11, is produced by fermentation of a microorganism belonging to the genus Micromonospora which is capable of producing DC-11 in a nutrient medium. At the completion of culturing, DC-11 is isolated from the culture liquor by known means, such as by ion exchange resin treatment.

DC-11 exhibits antibacterial activity and is, therefore useful to clean and sterilize laboratory glassware and surgical instruments and may also be used in combination with soaps, detergents and wash solutions for sanitary purposes. The compound is also expected to be useful in the treatment of bacterial infections in animals due to its antibacterial properties.

DESCRIPTION OF THE INVENTION

DC-11 is a novel composition of matter having antibacterial activity. The compound is characterized by the following physicochemical properties:

(1) Melting point: 225°–228° C. (Decomposition)

(2) Elementary analysis: H=6.9%, C=59.0%, N=2.0%

(3) Infrared absorption spectrum measured in KBr tablet as shown in FIG. 1.

(4) Ultraviolet absorption spectrum in methanol as shown in FIG. 2.

Figure 3A:
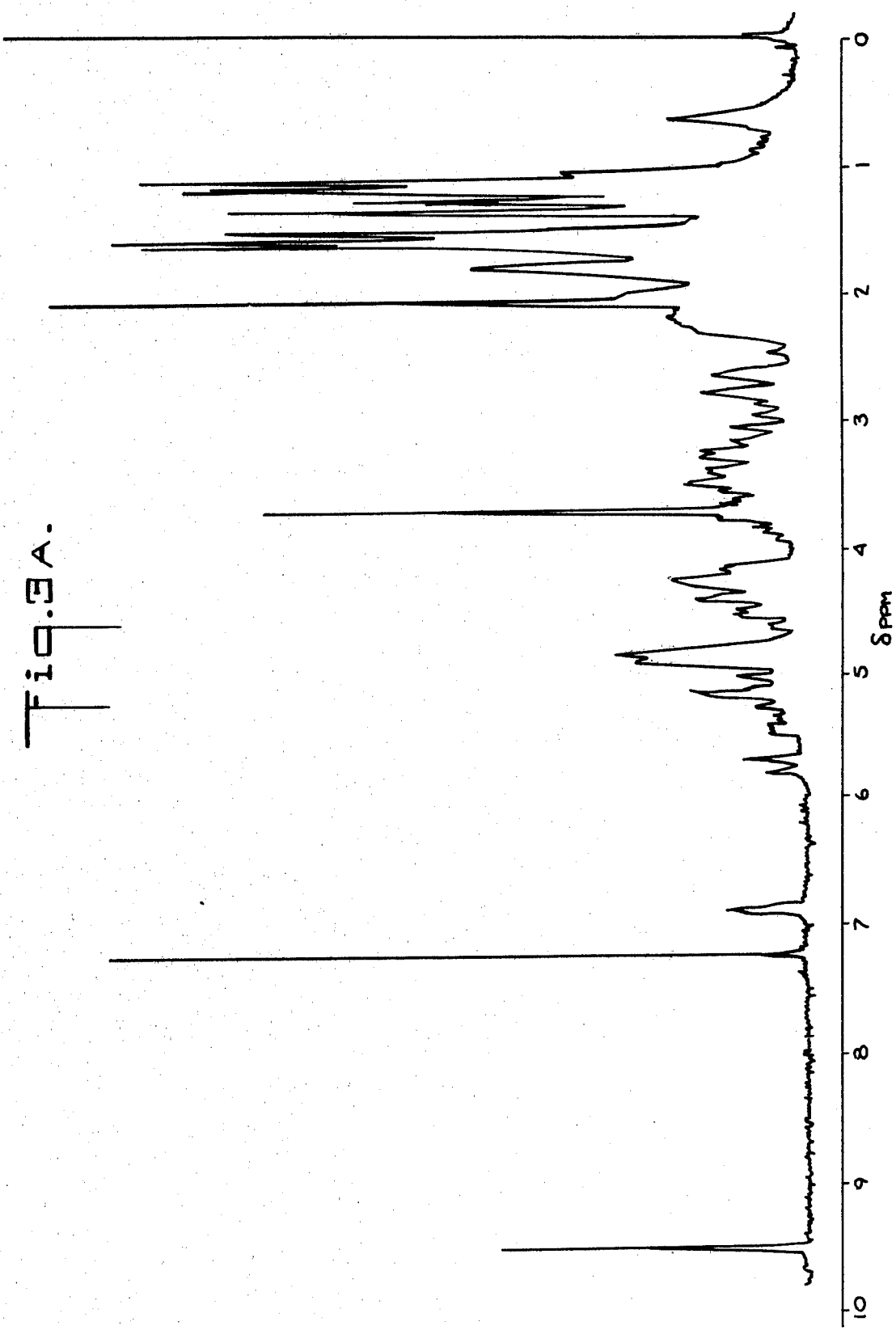

(5) The proton magnetic resonance spectrum (PMR) of DC-11, as shown in FIG. 3, was obtained in CDCl$_3$ as the solvent and tetramethylsilan (TMS) as the internal standard at 100 MHz. Representative features of the spectrum were at: 9.62, 6.92, 5.87–2.26 (many peaks), 2.09, 1.82, 1.64, 1.60, 1.53, 1.36, 1.29, 1.27, 1.21, 1.18, 1.13, 0.63 (ppm).

Figure 4:
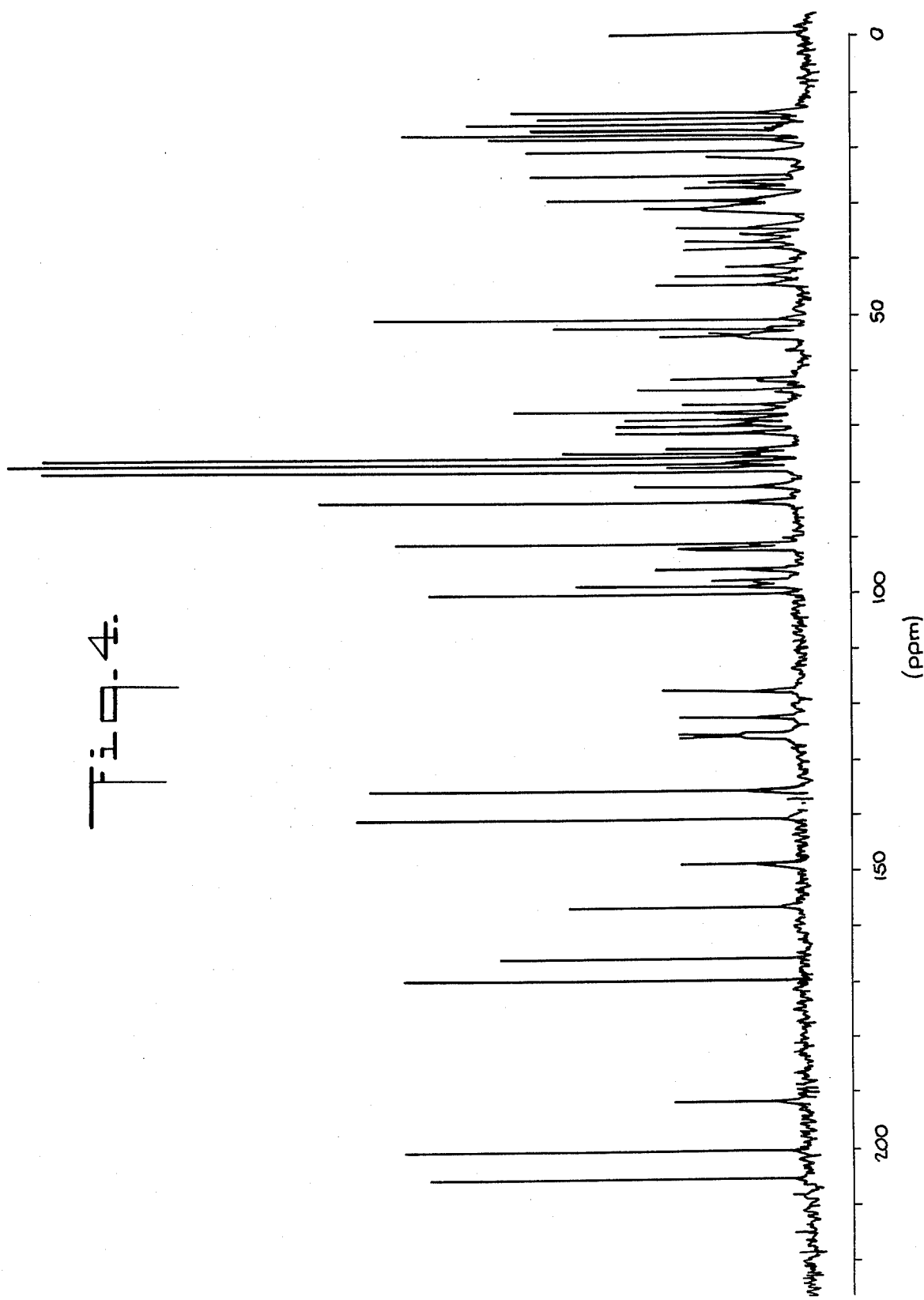

(6) The carbon magnetic resonance spectrum (CMR) of DC-11, as shown in FIG. 4, was obtained in CDCl$_3$ as the solvent and TMS as the internal standard at 25.1 MHz. Representative features of the spectrum were at: 14.0, 14.2, 15.1, 16.1, 16.9, 17.0–21.0 (about 5 peaks) 22.1, 25.3, 26.8–28.0 (about 2 peaks), 29.7, 31.2, 34.0–37.0 (about 3 peaks), 38.5, 41.8, 43.2, 44.9, 51.2, 52.8, 53.8, 54.3, 60.0–68.0 (about 4 peaks), 69.3, 70.0–78.0 (about 5 peaks), 81.1, 83.9, 84.3, 91.4, 91.5–100.0 (about 5 peaks), 100.8, 118.2, 123.0, 125.9, 126.3, 136.0, 136.3, 141.3, 149.6, 157.3, 166.5, 170.4, 192.6, 201.4, 206.4, (ppm).

(7) Specific optical rotation: $[\alpha]_D^{20} = -86.3°$ (C=1.0, acetone).

(8) Solubility:

DC-11 is soluble in methanol, ethanol, butanol, acetone, ethyl acetate and chloroform, slightly soluble in benzene and water, and insoluble in ethylether, petroleum ether and n-hexane.

Mass spectropic analysis does not disclose a clear molecular ion.

From the results of elementary analysis and CMR spectrum, DC-11 is considered to have the empirical formula $C_{64-72} H_{90-102} N_2 O_{26-30}$ and a molecular weight of 1204–1476.

As is illustrated by the following experimental analysis, it has been determined that the structure of DC-11 includes L-digitoxose and L-amicetose as constituents.

In this experimental analysis, 1.5 g of DC-11 is dissolved in a mixed solvent of 75 ml of 0.2 N HCl and 150 ml of acetone and the solution is refluxed for 17 hours. After the acetone is distilled away under reduced pressure, the resultant mixture is extracted with four 50 ml portions of chloroform.

The resultant water layer is concentrated to 10 ml under reduced pressure and the concentrate is passed through a column packed with the cation exchange resin, Dowex 1×4 (OH$^-$). The resin is then thoroughly washed with water. The eluate is concentrated under reduced pressure and the resulting residue is subjected to column chromatography using silica gel. The column is developed with a mixed solvent of chloroform and methanol (9:1 by volume) to obtain fractions containing L-amicetose and fractions containing L-digitoxose.

The former fractions are concentrated to obtain 218 mg of an oily substance. The latter fractions are concentrated to dryness to obtain 196 mg of a solid.

The oily substance is distilled at a pressure of 0.1 mm Hg to obtain a purified oil. The solid substance is recrystallized from a mixed solvent of n-hexane and acetone to obtain colorless prisms.

The physicochemical properties of the purified oil are as follows:

(1) Appearance: Colorless oil;

(2) Boiling point: 75° C./0.1 mm Hg;

(3) Specific optical rotation: $[\alpha]_D^{22} = -50.9°$ (c=1.08, acetone);

(4) The physicochemical properties of the 2,4-dinitrophenylhydrazone derivative obtained by reacting the oily substance with 2,4-dinitrophenylhydrazine are as follows:

Melting point: 160°–161° C.;

The PMR spectrum of the 2,4-dinitrophenylhydrazone derivative, obtained in d$_5$-pyridine as the solvent and TMS as the internal standard shows representative features at (δ, ppm);

1.56(d, 6.1, 3H), 2.20(m, 2H), 2.85(m, 2H), 3.94(m, 1H), 4.14 (dq, 6.1, 6.1, 1H), 7.91(d, 9.5, 1H), 7.96(t, 5.3, 1H), 8.29(dd, 9.5, 2.7, 1H), 9.04(d, 2.7, 1H).

Elementary analysis of 2,4-dinitrophenylhydrazone derivative Found (%): C=46.13, H=5.14, N=17.94; Calculated for $C_{12}H_{16}N_4O_6$: C=46.15, H=5.16, N=17.94.

From the foregoing, the oily substance is identified as L-amicetose.

The physicochemical properties of the prisms are as follows.

(1) Appearance: Colorless prisms;
(2) Melting point: 110°–112° C.;
(3) Specific optical rotation: $[\alpha]_D^{22} = -37.3°$ (c=1.11, methanol);
(4) The PMR spectrum of the substance, obtained in $CD_3OD$ as solvent and TMS as the internal standard, shows representative features at ($\delta$, ppm): 1.23(d, 6.1, 3H), 1.61(ddd, 13.7, 9.5, 2.8, 1H), 2.02(ddd, 13.7, 3.7, 2.8, 1H), 3.14(dd, 9.5, 3.2, 1H), 3.77 (dq, 9.5, 6.1, 1H), 4.00(ddd, 3.7, 3.2, 2.8, 1H), 5.06 (dd, 9.5, 2.4, 1H).
(5) Elementary analysis Found (%): C=48.47, H=8.34; Calculated for $C_6H_{12}O_4$: C=48.64, H=8.16

From the foregoing, the prisms are identified as L-digitoxose.

While not wishing to be bound thereby, it is theorized that based on additional studies involving DC-11, it is in salt form and its free form, designated tetrocarcin A, has the following structural formula:

to hydrolysis to obtain L-amicetose, L-digitoxose and a compound represented by the following formula:

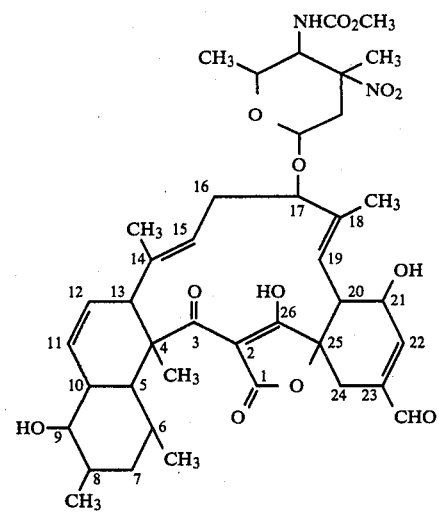

Based on the physicochemical properties of tetrocarcin A, DC-11 and antlermicin A (the free form of which is

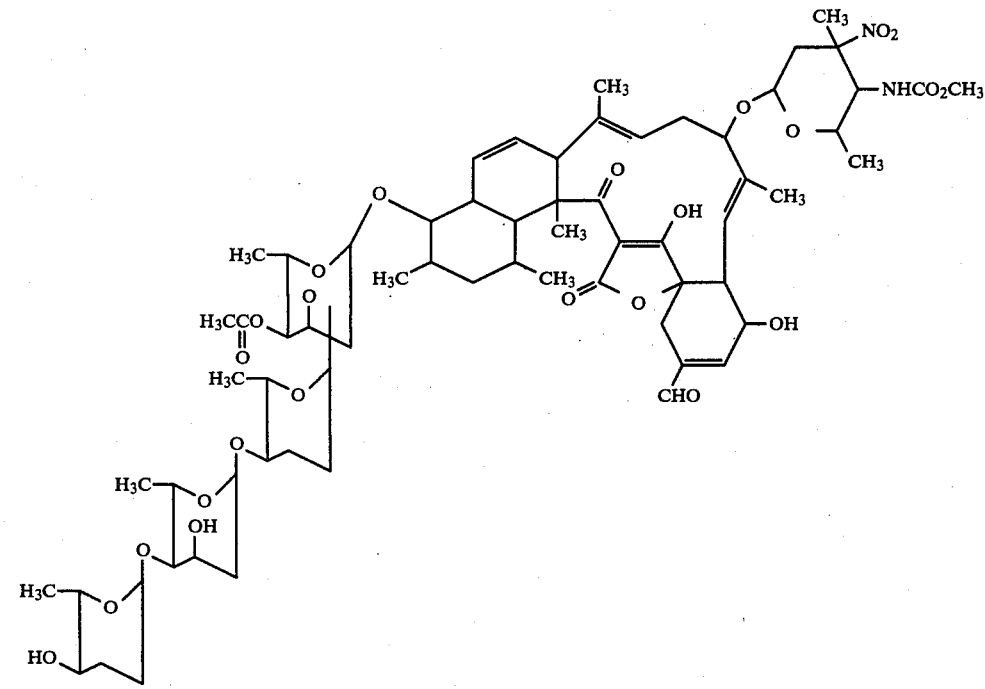

The forementioned studies involved obtaining tetrocarcin A by dissolving DC-11 in ethyl acetate, washing the solution with dilute hydrochloric acid and subjecting the resulting solution to column chromatography using silica gel. The resulting tetrocarcin A is subjected considered to be identical to tetrocarcin A; see *J. Antibiotics*, 33, 244–246, 1980) as shown in Table A below and the results of the hydrolysis above referred to, the above formula for tetrocarcin A was obtained.

TABLE A

Figure 1A:
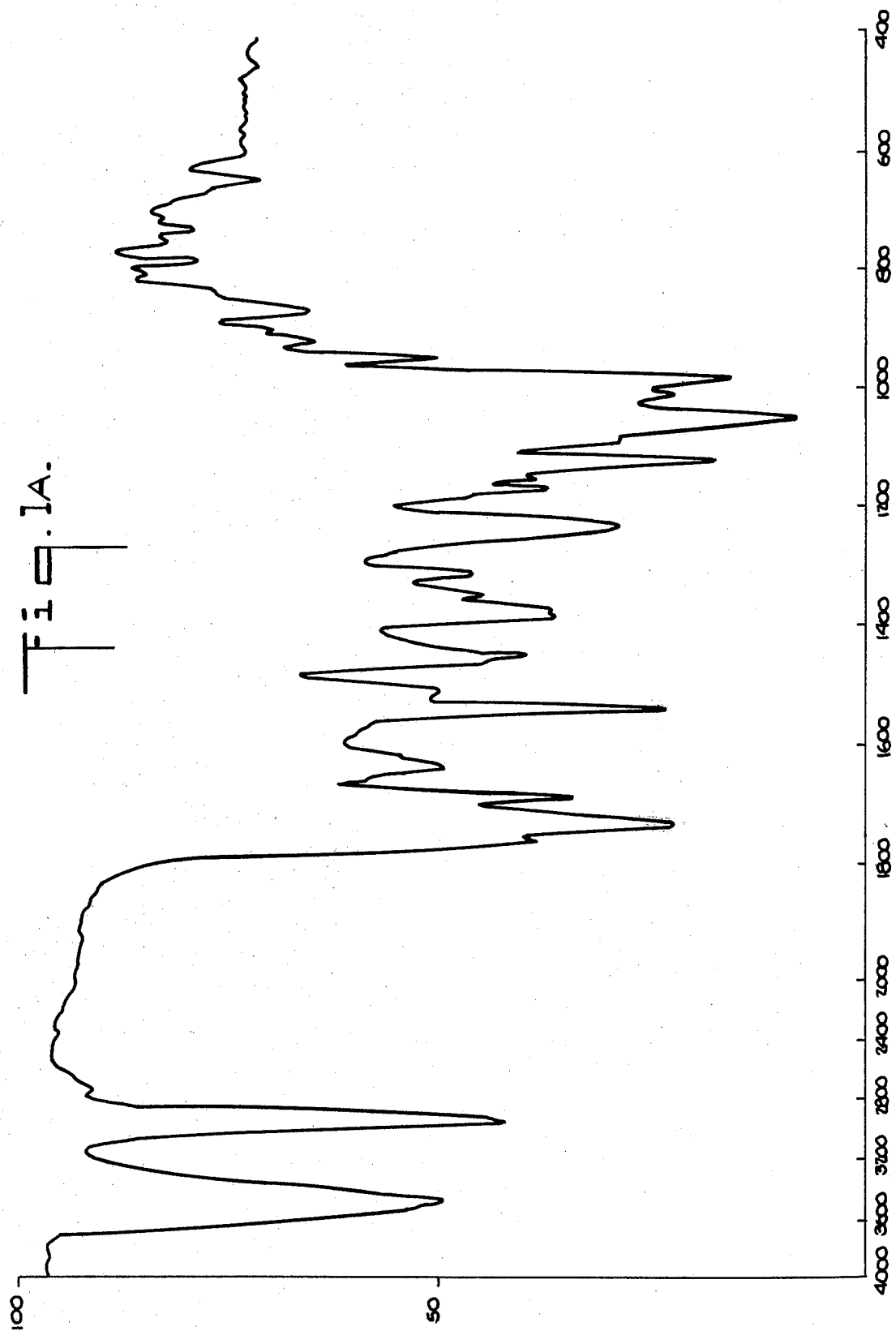

| | | DC-11 | Tetrocarcin A | Antlermicin A |
|---|---|---|---|---|
| (1) | Melting point (°C.) | 225–228 | 198–202 | 199–204 |
| (2) | Elementary analysis (%) | | | |
| | H | 6.9 | 7.5 | 7.20 |
| | C | 59.0 | 60.4 | 59.33 |
| | N | 2.0 | 2.1 | 1.98 |
| (3) | IR spectrum (in KBr tablet) | FIG. 1 | FIG. 1A | FIG. 2 of J. Antibiotics, supra |

TABLE A-continued

Figure 2A:
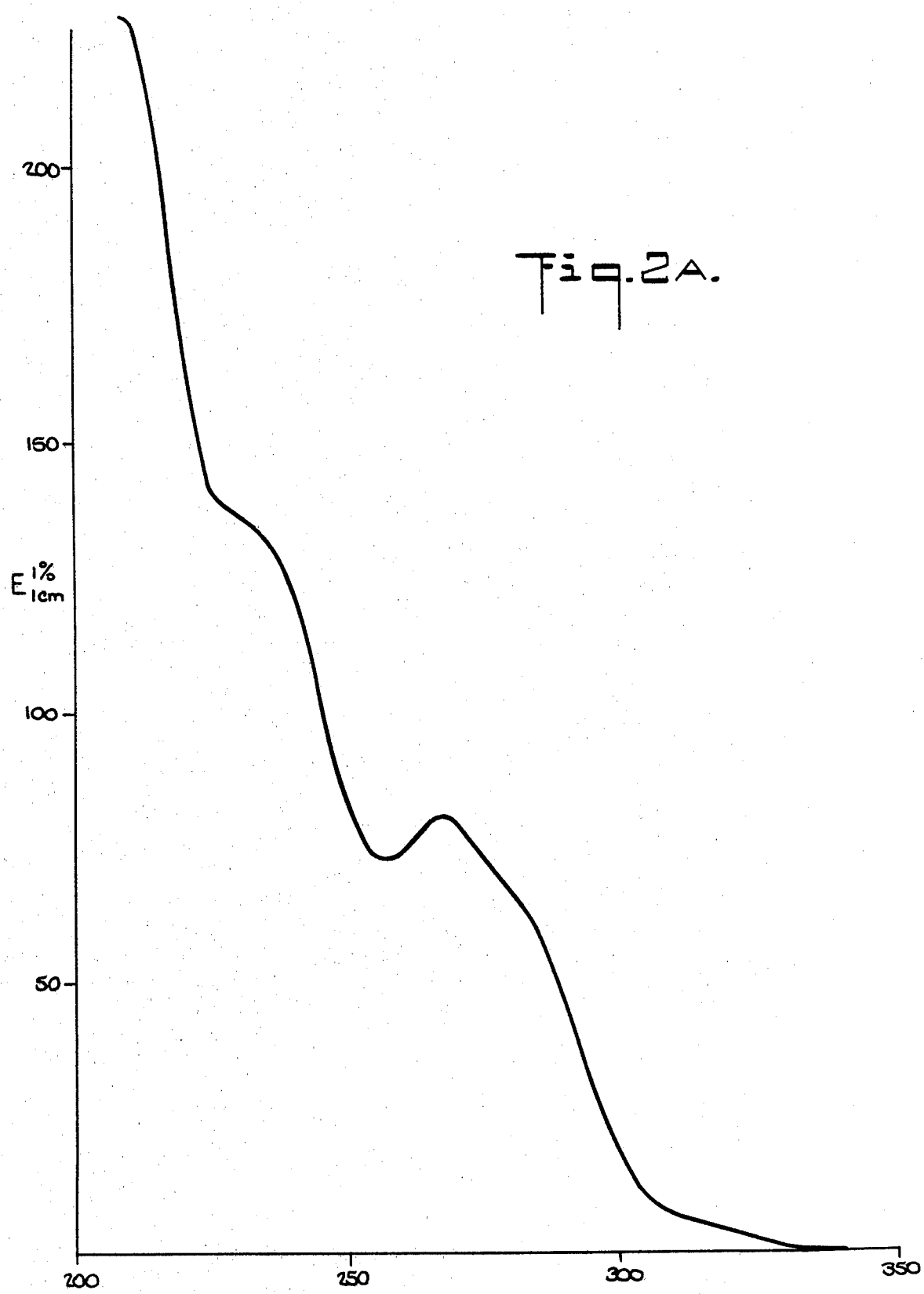
Figure 4A:
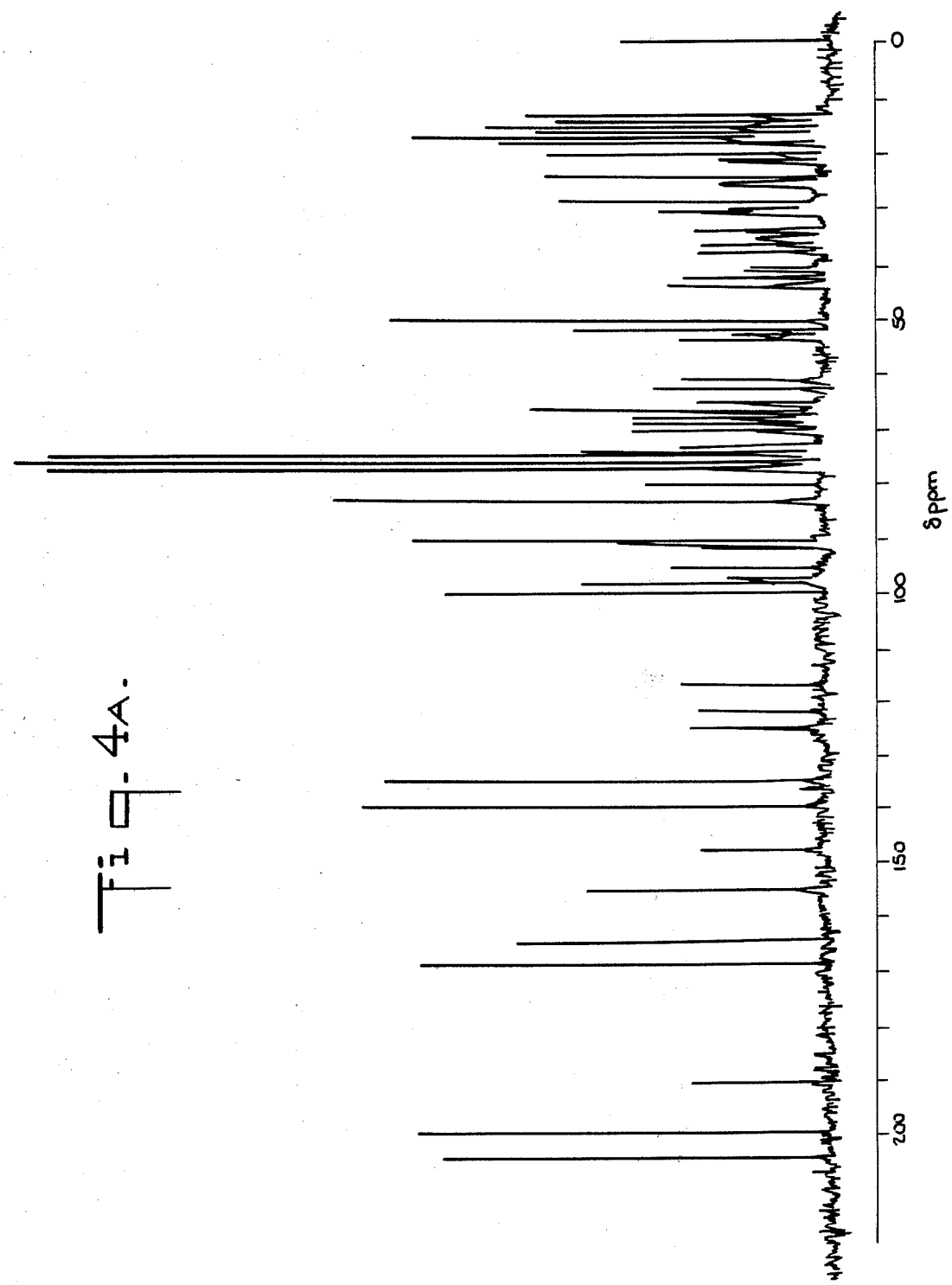

|   | DC-11 | Tetrocarcin A | Antlermicin A |
|---|---|---|---|
| (4) UV spectrum (in methanol) | FIG. 2 | FIG. 2A | FIG. 1 of J. Antibiotics, supra |
| (5) PMR spectrum (in CDCl$_3$) | FIG. 3 | FIG. 3A | — |
| (6) CMR spectrum (in CDCl$_3$) | FIG. 4 | FIG. 4A | FIG. 3 of J. Antibiotics, supra (in acetone) |
| (7) Specific optical rotation (c = 1.0, acetone) | $[\alpha]_D^{21}$ −86.3° | $[\alpha]_D^{21}$ −74.3° | $[\alpha]_D^{28}$ −67.6° (C = 1, methanol) |
| (8) Molecular weight |  | 1313 | 1306 |
| (9) Molecular form |  | C$_{67}$H$_{96}$N$_2$O$_{24}$ |  |

The Rf values of D-11 in silica gel thin layer chromatography (TLC) using various developers are set forth in the following Table 1.

TABLE 1

| Carrier* | Developer (V/V) | Rf |
|---|---|---|
| I | Benzene:Acetone (35:65) | 0.55 |
|  | Toluene:Acetone (4:6) | 0.48 |
|  | Chloroform:Methanol (9:1) | 0.60 |
| II | Chloroform:Dioxane (92.5:7.5) | 0.70 |
|  | Chloroform:Tetrahydrofuran (85:15) | 0.67 |
|  | Chloroform:Acetone (9:1) | 0.50 |
| III | Acetone:Dioxane: 10% Ammonium Acetate (5:5:1) | 0.35 |

*I: Silica gel for TLC, No. 5715, product of Merck & Co., Inc.
II: Silica gel for reversed phase TLC, No. 5747, product of Merck & Co., Inc.
III: Alumina for TLC, No. 5727, product of Merck & Co., Inc.

DC-11 is produced by culturing a microorganism belonging to the genus Micromonospora and which is capable of producing the active substances. A particularly preferred strain is *Micromonospora chalcea* KY 11091; and this type strain has been deposited with the culture collection of the Northern Utilization Research and Development Division, Agricultural Research Service, U.S. Department of Agriculture (formerly Northern Regional Research Agriculture), Peoria, Ill. 61604 and is available to the public under culture No. NRRL 11289.

The strain has also been deposited with the Fermentation Research Institute, Japan and assigned the registered number FERM-P No. 4458.

The KY 11091 strain is characterized by the following properties:

I. Morphology:

Well developed, branching, non-septate substrate mycelia having a diameter of about 0.5μ are formed but no true aerial mycelia are formed. Spores are formed very well and single spores are produced at the ends of simple sporophores (about 0.3–1.0μ in length) branched from the substrate mycelia. Many spores are formed around the ends of the substrate mycelia. Matured spores have a diameter of about 1.0μ and are spherical in shape.

When the strain is cultured in liquid medium, the growth is initially bright orange changing to brown to dark brown at the latter stages. Many spores are formed.

When the strain is cultured on agar media, a brick-red, glossy, waxy spore layer is formed on the medium on which the spores are readily formed.

II. Culture Characteristics

The degree of growth, color of substrate mycelium and soluble pigments when the KY 11091 strain is cultured on various media are set forth in the following Table 2. The color indications are given according to the classifications in the Color Harmony Manual, (Container Corporation of America). The characteristics are determined after culturing at 30° C. for 2 weeks.

TABLE 2

| Medium | Growth | Color | Soluble Pigments |
|---|---|---|---|
| Sucrose-Nitrate agar | Good, flat | Black-olive (1 po) | None |
| Glucose-Asparagine agar | Poor, flat | White (a) | None |
| Glycerine-Asparagine agar | Poor, flat | White (a) | None |
| Starch-Inorganic salt agar | Good, flat | Black-olive (1 po) | None |
| Tyrosine agar | Moderate | Black-olive (1 po) | None |
| Nutrient agar | Moderate, flat | Apricot (4 ca) | None |
| Oatmeal agar | Moderate, flat | Apricot (4 ca) | None |
| Yeast-Malt agar | Good, raised | Black-olive (1 po) | None |
| Peptone-Yeast agar | Moderate, flat | Orange (4 la) | None |

III. Physiological characteristics

The physiological characteristics of the KY 11091 strain are illustrated in the following Table 3 in which the optimum temperature is determined after 5 days of culturing and the action upon milk and the decomposition of cellulose are observed after one month of culturing. The other observations are based on culturing at 27° C. for two weeks.

TABLE 3

| (1) Utilization of Carbon Sources | |
|---|---|
| Carbon Source | Utilization |
| D-Arabinose | − |
| D-Xylose | + |
| D-Glucose | ++ |
| D-Fructose | + |
| Sucrose | ++ |
| Inositol | − |
| L-Rhamnose | − |
| D-Raffinose | ++ |
| D-Mannitol | − |
| Ribose | + |
| Salicin | + |
| L-Arabinose | + |
| Glycerol | ± |
| Melibiose | + |
| Liquefaction of gelatin | Negative |
| Liquefaction of milk | Positive |
| Peptonization of milk | Negative |
| Decomposition of cellulose | Little |

TABLE 3-continued

| (1) Utilization of Carbon Sources | |
|---|---|
| Carbon Source | Utilization |
| Hydrolysis of starch | Positive |
| Optimum growth pH | 6.6–7.5 |
| Optimum growth temperature | 28–38° C. |
| Formation of hyrosinase | None |
| Formation of melanoid pigments | None |

As apparent from the above observations, the KY 11091 strain does not form true aerial mycelia on agar and forms a single spore on substrate mycelia. By analysis of cell wall, it is determined that the strain contains mesodiaminopimelic acid. On the basis of the above observations and the descriptions of Bergey's Manual of Determinative Bacteriology, 8th. edition, 846–849 and International Journal of Systematic Bacteriology, vol. 21, No. 3, 248–253, the strain is classified as belonging to the species *Micromonospora chalcea,* and this strain, in a biologically pure culture, produces recoverable amounts of DC-11 when fermentated.

As is the case with other strains of the Actinomycetes, the microorganism useful in carrying out the present invention can be mutated by artifical means such as ultraviolet irradiation, $Co^{60}$ irradiation, X-ray irradiation and the action of various mutation-inducing chemicals such as N-methyl-N'-nitro-N-nitrosoguanidine, etc. Accordingly, any strain, even if thus mutated, is contemplated as appropriate for the present invention insofar as it has the ability to produce the compound DC-11.

Generally, conventional methods for culturing Actinomycetes may be employed in the process of the present invention. Thus, various nutrient sources may be used for the culture medium. Appropriate carbon sources include glucose, starch, mannose, dextrin, fructose, sucrose, molasses, etc. either alone or in combination. Hydrocarbons, alcohols, organic acids, etc. may also be used depending upon the assimilability possessed by the microorganisms to be used. As inorganic and organic nitrogen sources, ammonium chloride, ammonium sulfate, urea, ammonium nitrate, sodium nitrate, may be used either alone or in combination or natural nitrogen sources such as peptone, meat extract, yeast extract, dry yeast, corn steep liquor, soybean powder, casamino acid, soluble vegetable protein, etc. are appropriate. If necessary, inorganic salts such as sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate, copper sulfate, etc. may be added to the medium. Moreover, organic and inorganic materials such as vitamin $B_1$, biotin, etc. which promote the growth of the particular strain and enhance the production of DC-11 may be added to the medium.

A liquid culturing method, particularly a submerged stirring culturing method is most suitable. Culturing temperatute is 25°–40° C., preferably 28°–38° C., and the pH is controlled at 4–10, preferably 6–8 with aqueous ammonia, ammonium carbonate solution, etc. Usually, after 1 to 7 days of liquid culturing, DC-11 is formed and accumulated in the culture liquor. When the yield of DC-11 in the culture liquor reaches a maximum, culturing is discontinued and the desired product is isolated and purified from the culture liquor after the microbial cells have been removed such as by filtration.

Isolation and purification of DC-11 are carried out by methods usually used for the isolation and purification of microbial metabolic products from a culture liquor. For example, the cell-free culture filtrate (pH 6.0) is passed through a column packed with nonionic porous resin, such as HP-20 (trademark, Mitsubishi Chemical Industries) to adsorb active principles; and the active principles are desorbed using methanol, acetone, ethyl acetate, or the like. The resultant eluate is concentrated to dryness and the residue is dissolved in water. Then the solution is passed through a column packed with active carbon and elutation is carried out with an organic solvent such as ethyl acetate. The eluate is concentrated to dryness and the residue is dissolved in chloroform. The solution is then passed through a column packed with silica gel suspended in chloroform, whereby yellowish impurities are removed. Elution is then carried out with a mixed solvent to chloroform and methanol (98:2 by volume), and the eluate is concentrated to dryness to obtain the active compound. The same chromatography as described above or chromatography using a cross-linked polysaccharide dextran such as Sephadex LH-20 (trademark, Pharmacia Fine Chemicals Inc., Sweden) may be repeated for further purifying the desired product. The thus obtained DC-11 has the physicochemical properties described above.

The biological properties of DC-11 are illustrated below.

The in vitro antibacterial spectra of DC-11 determined by the disc method (pH 8.0) is illustrated in the following Table 4.

TABLE 4

| Microorganim | Minimum Inhibitory Concentration (μg/ml) MIC |
|---|---|
| *Staphylococcus aureus* ATCC 6538 P | 20 |
| *Bacillus subtilis* No. 10707 | 0.1 |
| *Klebsiella pneumoniae* ATCC 10031 | >100 |
| *Escherichia coli* ATCC 26 | >100 |
| *Shigella sonnei* ATCC 9290 | >100 |
| *Salmonella typhosa* ATCC 9992 | >100 |

The acute toxicity ($LD_{50}$) of DC-11 is 54 mg/Kg when the test compound is administered intraperitoneally to mice.

Additional activity of DC-11 is as follows:

(1) Effect on sarcoma 180 ascites tumor.

Six male ddY-strain mice having a weight of 20 g are used for each group as test animals; and $5 \times 10^6$ cells of Sarcoma 180 ascites tumor are implanted in the animals. After 24 hours following implantation, 0.2 ml phosphate buffered saline (PBS) containing DC-11 in various concentrations is administered intraperitoneally. PBS comprises 0.8 g/dl NaCl, 0.02 g/dl KCl, 1.15 g/dl $Na_2HPO_4$, 0.02 g/dl $KH_2PO_4$ (pH 7.2).

For comparison, 0.2 ml PBS solution containing mitomycin C is administered to a group of amimals intraperitoneally at the same time as the test compound.

Seven days after implantation, the average tumor volume ($mm^3$) and T/C (T: average tumor volume of test compound, C: that of control) are determined. The results are shown in the following Table 5.

TABLE 5

| Test Compound | Dosage (mg/Kg) | V ($mm^3$) | T/C |
|---|---|---|---|
| Control | 0 | 1405 | — |
| DC-11 | 25 | 1096 | 0.78 |

TABLE 5-continued

| Test Compound | Dosage (mg/Kg) | V (mm³) | T/C |
|---|---|---|---|
| DC-11 | 50 | 730 | 0.52 |
| DC-11 | 70 | 590 | 0.42 |
| Mitomycin C | 4.2 | 450 | 0.32 |

V: average tumor volume (2) Effect on Lymphocytic leukemia P-388 tumor.

Five male $CDF_1$ mice having a weight of about 22 g are used for each group as test animals, and $1 \times 10^6$ cells of Lymphocytic leukemia P-388 tumor are implanted intraperitoneally in the test animals. Twenty-fours hours following implantation, 0.2 ml PBS solution containing DC-11 in various concentrations is administered intraperitoneally.

For comparison, 0.2 ml PBS solution containing mitomycin C is administered to a group of test animals intraperitoneally at the same time as the test compound.

The average survival period (ASP: days) and T/C (T: average survival days of the groups administered with test compound, C: average survival days of the control group) after implantation are shown in the following Table 6.

TABLE 6

| Test Compound | Dosage (mg/Kg) | ASP (days) | T/C |
|---|---|---|---|
| Control | 0 | 9.4 | — |
| DC-11 | 6.25 | 11.2 | 1.20 |
| DC-11 | 12.5 | 13.4 | 1.43 |
| DC-11 | 25.0 | 13.0 | 1.38 |
| Mitomycin C | 4.2 | 14.2 | 1.51 |

As is apparent from the foregoing, DC-11 is useful as an antibacterial agent, for example, in the form of pharmaceutical preparations incorporating the active substance in admixture or conjunction with an organic or inorganic solid or liquid pharmaceutical excipient suitable for enteral, parenteral or local administration. Suitable excipients are substances which do not react with DC-11, for example, water, gelatin, saline, lactose, starch, alcohol, magnesium sterate, talcum, vegetable oil, polyalkyleneglycols or other known excipients. The pharmaceutical preparations may be formulated as tablets, capsules or liquids such as solutions, suspensions or emulsions. DC-11 is most suitably administered as an injection. DC-11 may be effectively administered on a daily basis in dosages of from about 0.1 to 0.5 mg/Kg of body weight.

When DC-11 is used as an injection, a solution or suspension for injection is prepared by dissolving DC-11 in an organic solvent or by using a surfactant such as HCO-60, Tween 80, or the like. When a surfactant is used, DC-11 is, for example, dissolved in 2500-5000 times weight amount of ethanol based on the weight of DC-11 and then 3-5 times weight amount of surfactant based on the weight of DC-11 is added. The enthanol is then removed in vacuo and sterilized normal saline solution is added to the residue to obtain an injectable solution.

Certain specific embodiments of the present invention are illustrated by the following representative examples wherein the presence of DC-11 is monitored by bio-assay using *Bacillus subtilis* No. 10707.

EXAMPLE 1

In this example, *Micromonospora chalcea* KY 11091, NRRL 11289, is inoculated into a 2 L-Erlenmyer flask containing 300 ml of seed medium comprising 4 g/L KCl, 0.5 g/L $MgSO_4.7H_2O$, 1.5 g/L $KH_2PO_4$, 5.0 g/L $(NH_4)_2SO_4$, 20 g/L sucrose, 10 g/L fluctose, 10 g/L glucose, 5.0 g/L corn steep liquor and 20 g/L $CaCO_3$ (pH 7.0) and cultured at 30° C. for 48 hours with stirring (220 r.p.m.). Then, 0.75 L. of the thus obtained seed culture is transferred to a 30 L-jar fermenter containing 15 L of a fermentation medium comprising 40 g/L soluble starch, 8 g/L yeast extract, 0.09 g/L $MgSO_4.7H_2O$, 0.15 g/L $KH_2PO_4$, 0.21 g/L $K_2HPO_4$, 10 mg/L vitamin $B_1.HCl$, 30 μg/L biotin, 10 mg/L $FeSO_4.7H_2O$, 30 mg/L $CaCl_2$, 4 mg/L $MnSO_4$, 30 mg/L $ZnSO_4.7H_2O$ and 2 mg/L $CuSO_4.5H_2O$. The pH of the medium is adjusted to 7 with NaOH before sterilization. Culturing is carried out at 30° C. with aeration and agitation (15 L/min, 250 r.p.m.) for 72 hours without controlling the pH of the medium.

The resulting culture liquor is filtered to obtain 13 L of filtrate. The filtrate is passed through a column packed with 1 L of non-ionic porous resin HP-10 (trademark, Mitsubishi Chemical Industries) to adsorb the active principles. Then the resin is washed with water and 30% (V/V) acetone solution to remove the impurities. Elution is carried out with acetone and the acetone fractions are concentrated to dryness to obtain a residue which is then dissolved in 30% acetone solution. The resultant solution is charged to a column packed with 50 ml acetive carbon and the carbon is washed with 30% acetone solution. Elution is then carried out with acetone whereby most of the pigments which are present in the solution as impurities are removed. Active fractions are combined and concentrated to dryness and the residue is dissolved in about 10 ml of chloroform. The chloroform solution is charged to a column packed with 500 ml silica gel, Silic AR CC-4 (trademark, Mallinckrodt Co., U.S.A.) suspended in chloroform and washed with about 2 L of chloroform.

Then elution is carried out with a mixed solvent of chloroform and methanol (98:2 by volume) to obtain fractions containing DC-11. The fractions are concentrated to dryness to obtain 55 mg of crude preparate. The preparate is subjected to chromatography using silica gel as described above to obtain 32 mg of a purified powder, the physicochemical properties, antibacterial activity and other properties of which agree with the properties described above.

EXAMPLE 2

In this example an injectable form of DC-11 is prepared by dissolving 10 mg of DC-11 obtained in Example 1 in 50 ml ethanol. Then, 30 mg of HCO-60 Nikkol (Product of Nikko Chemicals Co.) is added to the solution and the mixture is stirred for 10 minutes. The ethanol is removed in vacuo and 10 ml of sterilized normal saline solution is added to the residue to obtain an injection solution.

What is claimed is:

1. A composition of matter, DC-11, characterized by:
Melting point: 225°-228° C. (decomposition)
Elementary analysis: H=6.9%, C=59.0%, N=2.0%
Infrared absorption spectrum measured in KBr tablet substantially as shown in FIG. 1;
Ultraviolet absorption spectrum in methanol substantially as shown in FIG. 2;
Proton magnetic resonance spectrum in $CDCl_3$ substantially as shown in FIG. 3;
Carbon magnetic resonance spectrum in $CDCl_3$ substantially as shown in FIG. 4; and Specific optical rotation: $[\alpha]_D^{20} = -86.3$ (C=1.0, acetone).

2. An antibacterial pharmaceutical composition which comprises an effective antibacterial amount of the composition of matter of claim 1 and a pharmaceutically non-toxic excipient.

3. A process for producing DC-11 as defined in claim 1 which comprises culturing a microorganism having the identifying characteristics of *Micromonospora chalcea* KY 11091, NRRL 11289 in a nutrient medium until substantial biological activity is detected in the culture liquor and then isolating said compound DC-11 from the culture liquor.

4. A process according to claim 3, wherein said culturing is carried out at a temperature of 25°–40° C. for one to seven days at a pH of about 4 to 10.

* * * * *